United States Patent [19]

Strand

[11] Patent Number: 4,842,558
[45] Date of Patent: Jun. 27, 1989

[54] ELECTRICAL CONNECTOR

[75] Inventor: Jerome E. Strand, Hudson, Wis.

[73] Assignee: Minnesota Mining and Manufacturing Company, St. Paul, Minn.

[21] Appl. No.: 258,182

[22] Filed: Oct. 14, 1988

[51] Int. Cl.⁴ .......................................... H01R 4/50
[52] U.S. Cl. ................................................. 439/863
[58] Field of Search ............... 439/395, 399, 820, 842, 439/848–850, 863, 909

[56] References Cited

U.S. PATENT DOCUMENTS

| | | |
|---|---|---|
| 446,564 | 2/1891 | Bacon . |
| 1,536,688 | 5/1925 | Osborn . |
| 1,799,747 | 4/1931 | Harvey .................. 173/273 |
| 1,942,435 | 1/1934 | Loosbrock ............. 173/259 |
| 3,088,086 | 4/1963 | Crimmins .......... 439/863 X |
| 3,475,717 | 10/1969 | Lane ........................ 339/75 |
| 3,504,332 | 3/1970 | Mixon, Jr. ............. 339/273 |
| 3,624,590 | 11/1971 | Bolduc ............... 339/75 R |
| 3,725,853 | 4/1973 | McKeown et al. ..... 339/252 R |
| 3,824,529 | 7/1974 | Dorrell .................... 339/99 |
| 3,842,394 | 10/1974 | Bolduc ............... 339/75 R |
| 4,061,408 | 12/1977 | Bast et al. ............ 339/75 R |
| 4,393,584 | 7/1983 | Bare et al. ............... 29/877 |
| 4,401,356 | 8/1983 | Bare .................... 339/258 R |
| 4,466,687 | 8/1984 | Frantz .................... 439/395 |
| 4,515,669 | 5/1985 | Dimond et al. ......... 204/196 |
| 4,522,211 | 6/1985 | Bare et al. ............. 128/640 |
| 4,550,961 | 11/1985 | Aicher et al. ........ 339/14 R |
| 4,634,205 | 1/1987 | Gemra ................. 339/97 P |
| 4,657,023 | 4/1987 | Kuhn ..................... 138/640 |
| 4,679,563 | 7/1987 | Wada et al. ........... 128/640 |
| 4,694,835 | 9/1987 | Strand ................... 128/640 |
| 4,696,532 | 9/1987 | Mattis ................... 439/863 |
| 4,700,997 | 10/1987 | Strand ................... 439/372 |

FOREIGN PATENT DOCUMENTS 272953 7/1965 Australia ............... 439/863

Primary Examiner—Eugene F. Desmond
Attorney, Agent, or Firm—Donald M. Sell; Walter N. Kirn; Stephen W. Bauer

[57] ABSTRACT

An electrical connector for releasably connecting a flat terminal, such as the terminal of a biomedical electrode, to an electric wire. The connector comprises a housing having a passageway extending substantially therethrough, and an actuator in the passageway. The housing has a first terminal-engaging surface defining one side of the passageway, and the actuator has a second terminal-engaging surface complementary to the first terminal-engaging surface of the housing. The actuator is slidable generally diagonally of the passageway in the housing between an open position, wherein the first and second terminal-engaging surfaces are spaced apart a distance at least as large as the thickness of the electrode terminal so that the terminal may be placed between the surfaces, and a wedged position, wherein the first and second terminal-engaging surfaces are sufficiently close to clamp the terminal between the surfaces with the actuator being wedged against the terminal to retain the terminal in the connector.

14 Claims, 2 Drawing Sheets

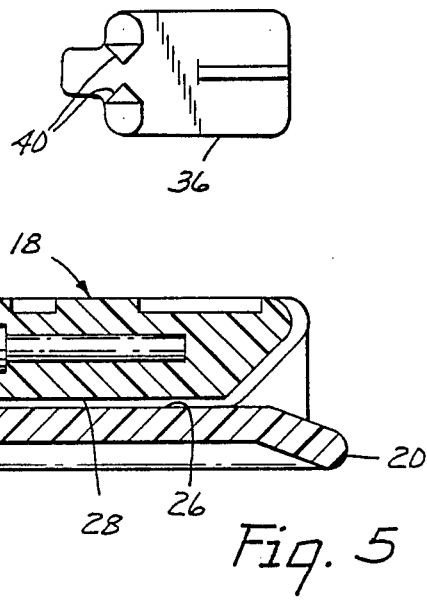
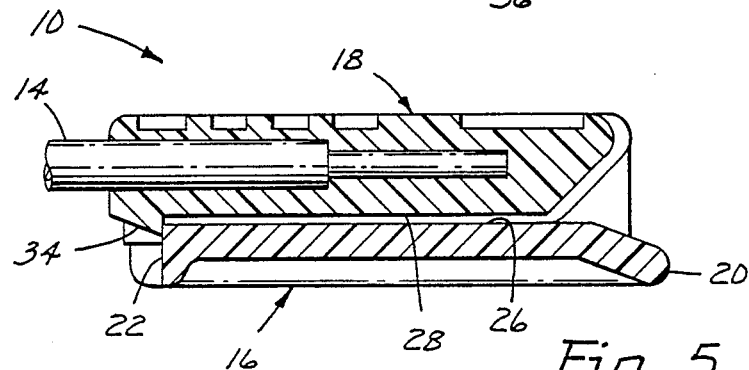
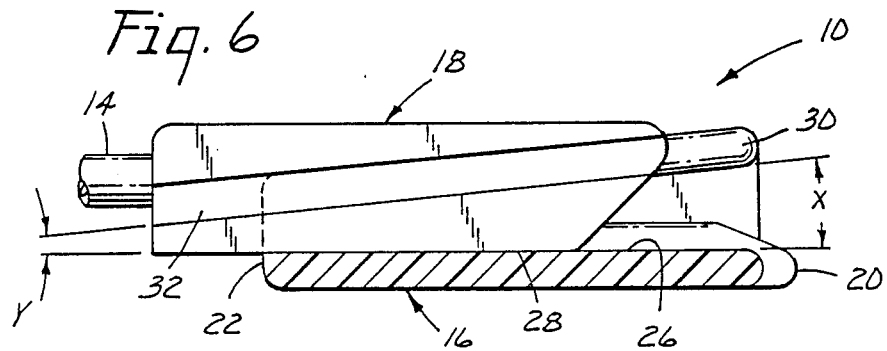
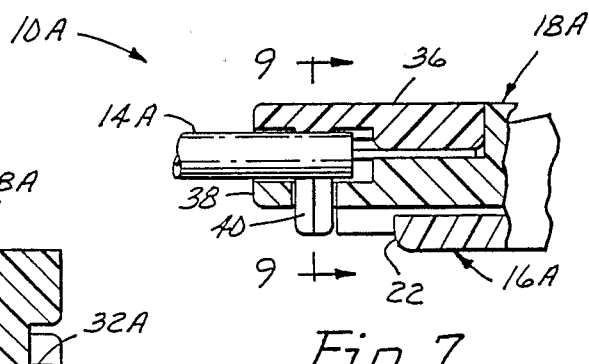
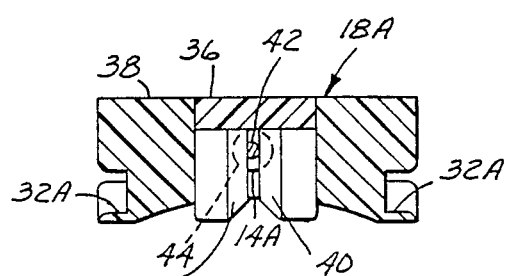

ELECTRICAL CONNECTOR

This invention relates generally to electrical connectors, and more particularly to an electrical connector for releasably connecting a flat terminal of a biomedical electrode to an electric wire.

BACKGROUND OF THE INVENTION

Biomedical electrodes are commonly used for transcutaneous monitoring of variations in electrical potential associated with muscular activity, such as the pumping of a heart, and for grounding patients during electrosurgery. One such electrode is described in coassigned U.S. Pat. No. 4,694,835, and has a flat or tabular terminal for conductively attaching the electrode to electric wire leading to some type of instrumentation, such as an electrocardiograph. The tabular terminal comprises a flat electrical conductor bonded to a nonconductive backing having a continuous coating of a suitable biocompatible pressure sensitive adhesive, thereby forming nonconductive and conductive surfaces along opposite sides of the terminal.

Typically, the electric wire has been attached to terminals of this type via an "alligator" clip having opposed pivoting metal jaws with serrated, i.e., saw-shaped, teeth for holding a terminal. The jaws are spring-loaded to a closed position for clamping the terminal between the jaws, and are movable to an open position for placing the clip on the terminal. Problems with alligator clip connections include "artifacts" in or interference with the signal from the electrode caused by movement of the clip relative to the tab, and insufficient surface contact with the electrode terminal, which among other things contributes to the difficulty with interference. Another problem is that the springs providing the closing force in alligator clips have been insufficiently strong to prevent inadvertent disconnection due, for example, to movement of the patient. This problem is particularly troublesome when the patient is being monitored by automatic or semi-automatic instruments without immediate supervision. Other problems with alligator clips include that they are made of radiopaque materials and have widely varying profiles, thereby complicating interpretation of X-ray photographs made with the clips in place. Moreover, the sharp teeth of the jaws of the alligator clip can damage the conductive layer of the electrode terminal.

Coassigned U.S. Pat. No. 4,700,997 describes a push-button actuated electrical connector comprising upper and lower jaws spring-biased to an open position where a flat biomedical electrode terminal may be placed between the jaws, and a push-button actuator slidable in a housing along the upper jaw. The push-button actuator is movable along guiding cam-type surfaces from a release position where the jaws are not forced toward one another to a closed position where the actuator compresses the jaws toward one another to clamp the terminal between the jaws. The actuator may be released by moving it to the release position with a finger.

Coassigned U.S. Pat. No. 4,061,408 describes a connector for a plate electrode used in electrosurgery employing flexible generally U-shaped sheet material, the legs of which are forced together by a lever to hold a grounding plate electrode.

U.S. Pat. Nos. 4,522,211 and 4,393,584 describe several types of medical electrode connectors employing, among other things, a "spring-type clip terminal" or terminals for attaching the connector to a medical electrode.

U.S. Pat. No. 4,550,961 describes an electrosurgical electrode connector comprising upper and lower non-conductive connector plates interconnected by a hinge, and a two-legged contact spring biasing the connector plates apart. The connector plates are held together by a releasable latch mechanism on the upper plate that engages two connector posts extending upwardly from the lower plate through a connection tab of the electrode.

U.S. Pat. No. 3,842,394 describes an electrical connector for a plate electrode used in electrosurgery comprising two separable jaws spring-biased apart, and an overcenter-type releasable locking structure for moving the jaws together to clamp the electrode. U.S. Pat. No. 3,624,590 describes a clamp for disposable ground plate electrodes used in electrosurgery comprising two jaws pivotably interconnected and spring-biased together to clamp the electrode. The jaws may be separated to release the electrode by pushing two levers extending from the jaws together.

U.S. Pat. No. 4,515,669 describes an internal connection for a tubular anode of the type used for cathodic protection. The connection includes a pair of opposing wedge blocks that are adapted to tightly wedge together to form an electrical connection. The blocks include a corresponding tongue-and-slot arrangement in the inter-engaging faces of the blocks for positioning them relative to one another.

U.S. Pat. No. 3,504,332 describes a "multi-tap" electrical connector for underground connection of a number of cables to secondary cables designed for use in electricity transmission and distribution. The connector employs a wedge member for wedging the end of each electrical cable to the body of the connector. U.S. Pat. No. 1,942,435 describes a connection for a battery terminal post employing a wedge for engaging and holding the terminal post.

U.S. Pat. No. 4,634,205 describes conductor splicing devices for splicing aerial drop wires comprising a housing having tapered passageways for receiving the wires being spliced, and a wedge for each passageway which is driven into the passageway to press the wire against insulating-piercing terminals and hold the wires in the passageway.

U.S. Pat. No. 4,696,532 describes a connector for connecting the center conductor of coaxial cable to a junction box. The connector employs an axial spring sleeve having a conical section received in a complementary conically-shaped hole in a sleeve held in the connector. The arrangement is such that if the center conductor is pulled away from the connector, the conical section of the spring sleeve is pulled further into the sleeve held in the connector, thereby increasing the clamping force holding the center conductor in the connector.

In the biomedical connectors discussed above, the strength or tenacity of the grip is substantially constant regardless of any movement of the connector or tension in the electric wire. The tenacity of the grip does not increase in such connectors when the electric wire is jerked or otherwise tensioned. Moreover, these biomedical connectors must be either manually locked on the terminal by pushing a button or lever, or they include some type of spring-biasing mechanism for biasing the connector to its locked position. Either approach has shortcomings. Manually-actuatable mechanisms may be inadvertently left unlocked, and are frequently an annoying nuisance to lock. The spring-biasing mechanism may be inadvertently forced open against the spring bias in some situations, and weak spring mechanisms may result in unacceptable connections.

In the connectors described above that are not designed for use in the medical field, the wedges or tapered members are jammed into passageways to hold wires, cables or other members in the connector, and it would be time-consuming and annoying to manually jam such wedges in a biomedical connector, which may be used in situations where time is critical and unnecessary annoyances are particularly undesirable. Generally, these wedges are not readily reversible for releasing the wire, cable or other member from the connector. In addition, these wedges are separable from the connectors, and are likely to be lost or misplaced when needed.

SUMMARY OF THE INVENTION

This invention provides an electrical connector useful for releasably connecting a flat electrode terminal to an electric wire; that is designed to be self-locking and secure to prevent inadvertent disconnection; that may be locked by pulling the electric wire in a direction away from the electrode; that minimizes or eliminates undesirable connector-generated interference with a signal being transmitted between the electrode and wire; and that is easy to use and inexpensive to manufacture.

Generally, the connector of the invention comprises a housing, an actuator and means for conductively-attaching an electric wire to the connector. The housing has a passageway extending substantially therethrough defining a longitudinal direction, and a first terminal-engaging surface defining at least a portion of the passageway. The actuator has a second terminal-engaging surface complementary to the first terminal-engaging surface of the housing. Cooperable positioning means is provided for slidably positioning the actuator in the passageway of the housing such that the actuator is slidable generally diagonally relative to the passageway between an open position and a wedged position. At the open position, the first and second terminal-engaging surfaces are spaced apart a distance at least as large as the thickness of the terminal so that the terminal may be placed between the surfaces. At the wedged position, the first and second terminal-engaging surfaces are sufficiently close to clamp the terminal between the surfaces with the actuator being wedged against the terminal to retain the terminal in the connector.

Other features will be pointed out hereinafter.

BRIEF DESCRIPTION OF THE DRAWINGS

The invention will be further described with reference to the drawings wherein corresponding reference characters indicate corresponding parts throughout the several views of the drawings, and wherein:

FIG. 5 is a cross-sectional view similar to FIG. 4, showing the actuator in an open position;

FIG. 6 is a cross-sectional view along line 6—6 of FIG. 3, showing the actuator being wedged against a housing of the connector;

FIG. 7 is a partial side view of another embodiment of an actuator of the invention, with portions being broken away to illustrate an electrical wire fastener;

FIG. 8 is bottom plan view of the wire fastener of FIG. 7; and

FIG. 9 is a cross-sectional view along line 9—9 of FIG. 7.

DETAILED DESCRIPTION

Figure 1:
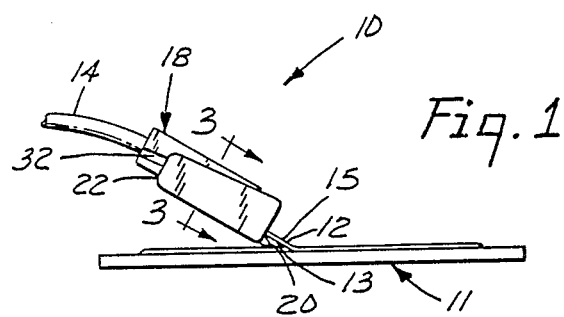
FIG. 1 is a side view of an electrical connector of the invention in use.

As shown in FIG. 1, an electrical connector of the invention is designated in its entirety by the reference numeral 10, and is useful for releasably connecting a flat terminal, such as a flat terminal 12 of a biomedical electrode 11 of the type described in coassigned U.S. Pat. No. 4,694,835 (which is incorporated herein by reference), to an electric wire 14. Biomedical electrodes of this type are used with electrocardiograph ("ECG") instruments to trace and monitor the electrical potentials associated with the operation of a heart. The tabular terminal 12 of the electrode 11 comprises a flat electrically-conductive layer 13 bonded to a nonconductive backing 15 having a continuous coating of a suitable biocompatible pressure sensitive adhesive (PSA), thereby forming a nonconductive surface and a conductive surface along the opposite sides or faces of the terminal. The electrical connector 10 may also be used with other types of electrodes having generally flat or tabular terminals, including terminals having conductive material on both sides or faces.

The connector 10 generally comprises a generally C-shaped housing 16 and an actuator 18 movable in the housing. The actuator 18 is formed of an electrically-conductive material, such as the carbon fiber reinforced polyphenylene sulfide sold under the trade designation "RTP 1385" or "RTP 1387" by the RTP Co., of Winona, Minn., or other suitable electrically-conductive polymers, although other materials, such as aluminum may also be suitable. The actuator 18 is molded with the electric wire 14 extending longitudinally-rearwardly (left in FIGS. 4-6) from the rear edge of actuator. The housing 16 may be molded of the same material as the actuator 18, although many nonconductive materials may also be suitable for the housing if the terminal 12 is placed in the passageway 24 with its conductive side facing the actuator. The housing 16 has forward and rearward edges 20 and 22, a passageway 24 extending through the housing between the forward and rearward edges, and a first terminal-engaging surface 26 in the passageway extending longitudinally of the passageway between the forward and rearward edges of the housing. The actuator 18 has a second terminal-engaging surface 28 complementary to the first terminal-engaging surface 26 of the housing 16.

Figure 4:
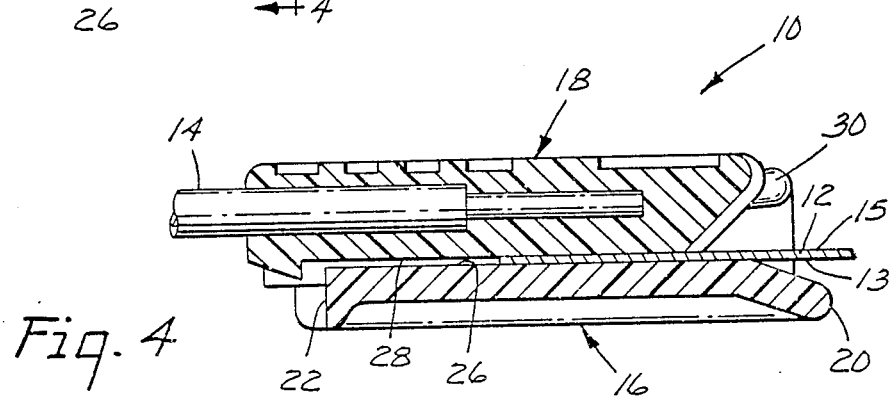
FIG. 4 is a cross-sectional view along line 4—4 of FIG. 3, showing an actuator of the connector in a wedged position.

Cooperable positioning means is provided for slidably positioning the actuator 18 in the passageway 24 of the housing 16 such that the actuator is slidable generally diagonally of the passageway between an open position (FIG. 5) and a wedged position (FIG. 4). For example, the cooperable positioning means may comprise opposed inwardly-extending ribs 30 in the housing 16, constituting first positioning means, and two corresponding channels 32, constituting second positioning means, in the actuator 18 slidably receiving the ribs for movement of the actuator between its open and wedged positions. When the actuator 18 is at its open position (FIG. 5), the first and second terminal-engaging surfaces 26 and 28 are spaced apart a distance at least as large as the thickness of the electrode terminal 12 so that the terminal may be placed between the surfaces. When the actuator 18 is at its wedged position (FIG. 4), the first and second terminal-engaging surfaces 26 and 28 are sufficiently close to clamp the electrode terminal 12 between the surfaces with the actuator being wedged against the terminal for securely retaining the terminal in the connector 10. Preferably, the ribs 30 and channels 32 are adapted to permit movement of the actuator 18 longitudinally-rearwardly from its open position toward its wedged position so that the actuator may be moved to its wedged position by pulling the electric wire 14 rearwardly (leftwardly in FIGS. 4–6).

More specifically, the ribs 30 of the housing 16 are formed along opposite sides of the passageway 24 and extend generally longitudinally of the passageway at an angle X (FIG. 6) relative to the first terminal-engaging surface 26, and the channels 32 are formed by walls in opposite sides of the actuator and extend at an angle Y relative to the second terminal-engaging surface 28 substantially equal to the angle X, with angles X and Y being appropriate to facilitate self-locking of the actuator in its wedged position in the housing. As used herein, the terms "self-locking" and "self-holding" refer to a tendency of the actuator to become and remain locked in the wedged position, as opposed for example to being "self-releasing" from the wedged position. It is believed that angles X and Y of between approximately 3–10 degrees (preferably 5 degrees), depending on the coefficients of friction of the terminal-engaging surfaces 26, 28 and terminal 12, provide sufficient frictional locking action for the actuator 18 to be self-locking or self-holding in the housing. The ribs 30 and channels 32 cooperate to permit movement of the actuator 18 between the open and wedged positions such that the first and second terminal-engaging surfaces 26 and 28 are substantially parallel throughout the movement.

Figure 2:
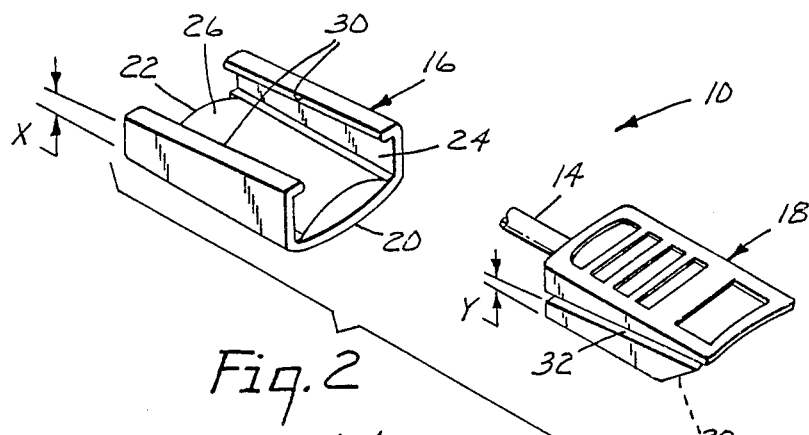
FIG. 2 is an enlarged exploded view of the connector of FIG. 1.
Figure 3:
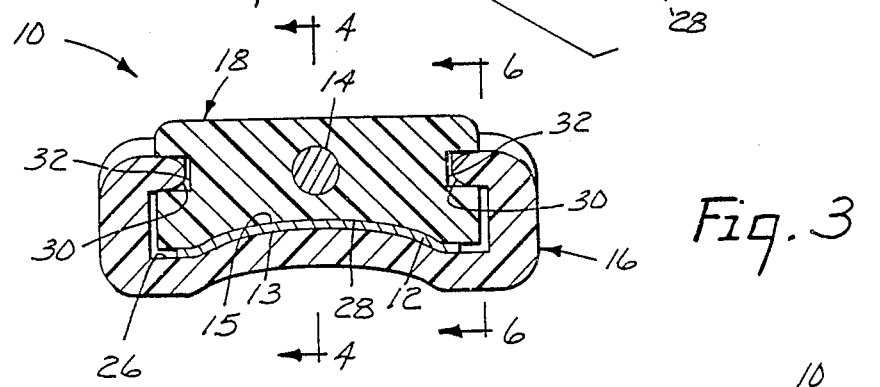
FIG. 3 is a cross-sectional view along line 3—3 of FIG. 1.

Preferably, the first and second terminal-engaging surfaces 26 and 28 are generally arcuate (FIGS. 2 and 3) with the axis of curvature of each surface extending generally longitudinally relative to the passageway 24 of the housing 16 (i.e., leftwardly or rightwardly in FIGS. 4–6). As shown in FIG. 3, the first terminal-engaging surface 26 is generally cylindrically convex, and the second terminal-engaging surface 28 is generally cylindrically concave and complementary to the first terminal-engaging surface. The curvature of the surfaces 26 and 28 increases the gripping tenacity of the connector 10 relative to grip of generally planar surfaces, and even provides some grip on the terminal 12 before the actuator 18 is moved to its wedged position, which is desirable in situations where the connector 10 is attached to the terminal without manually pulling the wire 14 or actuator rearwardly to lock the actuator. In this situation, it is believed that the actuator 18 will be generally self-locking on the terminal 12, since movement of the connector 10, wire 14 or electrode 11 will tend to cause the actuator to move to its wedged position.

Retaining means is provided for preventing separation of the actuator 18 from the housing 16. For example, the retaining means may comprise a lip 34 (FIG. 5) at the rearward end of the second terminal-engaging surface 28 of the actuator 18 for engaging the rearward edge 22 of the housing 16 when the actuator is in its open position, thereby preventing the actuator from moving forwardly (rightwardly in FIG. 5) beyond the open position. In addition, the actuator 18 is prevented from moving rearwardly (leftwardly in FIGS. 4–6) sufficiently to separate from the housing 16 by the second terminal-engaging surface 28 encountering the first terminal-engaging surface 26, as illustrated in FIG. 6.

FIGS. 7–9 illustrate another embodiment of an actuator 18A of the invention wherein the actuator includes wire-attaching means (e.g., a snap-fit fastener 36) for conductively-attaching an electric wire 14A to the body 38 of the actuator between the fastener and the body. Reference characters ending with an "A" in FIGS. 7–9 designate parts or features similar to those illustrated in the other figures having the same reference numerals not ending with an "A". The snap-fit fastener 36 and body 38 are formed of generally electrically-conductive material, such as the carbon-fiber-reinforced polyphenylene sulfide used for the actuator 18. The snap-fit fastener 36 includes opposed blades 40 (FIG. 8) spaced apart a distance no greater than the thickness of a conductive core 42 (FIG. 9) of the electric wire 14A that are adapted to cut through an electrical-insulating layer 44 (shown in phantom) coating the conductive core to provide a conductive path between the wire and the second terminal-engaging surface 28A. As shown in FIG. 7, the opposed blades 40 extend generally downwardly from the snap-fit fastener 36 beyond the second terminal-engaging surface 28A of the actuator 18A sufficiently to block forward (leftward in FIG. 7) movement of the actuator beyond the open position, it being understood that the blades constitute a second type of retaining means for preventing separation of the actuator from the housing.

As various changes could be made in the constructions described above without departing from the scope of the invention, it is intended that all matter contained in the description above or shown in the acompanying drawings be interpreted as illustrative and not in a limiting sense.

I claim:

1. An electrical connector for releasably connecting a substantially flat terminal to an electric wire, the connector comprising:

a housing having a passageway extending substantially therethrough defining a longitudinal direction, and a first terminal-engaging surface in the housing defining at least a portion of the passageway;

an actuator having a second terminal-engaging surface complementary to the first terminal-engaging surface of the housing;

means for conductively attaching the electric wire to the connector; and cooperable positioning means for slidably positioning the actuator along the passageway of the housing such that the actuator is slidable generally diagonally with respect to the passageway between an open position, wherein the first and second terminal-engaging surfaces are spaced apart a distance at least as large as the thickness of the terminal so that the terminal may be placed between the surfaces, and a wedged position, wherein the first and second terminal-engaging surfaces are sufficiently close to clamp the terminal between the surfaces with the actuator being wedged against the terminal to retain the terminal in the connector.

2. An electrical connector according to claim 1 wherein the cooperable positioning means includes first positioning means along opposite sides of the passageway extending generally longitudinally of the passageway at an angle no greater than approximately 10 degrees relative to the first terminal-engaging surface for slidably positioning the actuator, and second positioning means along opposite sides of the actuator extending at an angle relative to the second terminal-engaging surface substantially equal to the angle of the first positioning means relative to the first terminal-engaging surface, the first and second positioning means being cooperatively adapted to permit movement of the actuator between the open and wedged positions such that the first and second terminal-engaging surfaces are substantially parallel throughout the movement.

3. An electrical connector according to claim 2 wherein the angle of the first positioning means relative to the first terminal-engaging surface of the housing is approximately five degrees.

4. An electrical connector according to claim 2 wherein the first positioning means comprises ribs along the opposite sides of the passageway in the housing extending generally longitudinally of the passageway at the angle relative to the first terminal-engaging surface, and the second positioning means comprises walls forming channels along the opposite sides of the actuator complementary to the ribs of the housing, the ribs being slidably received in the channels for movement of the actuator between the open and closed positions.

5. An electrical connector according to claim 4 wherein the first and second terminal-engaging surfaces are generally arcuate with the axis of curvature of each surface extending generally longitudinally relative to the passageway of the housing.

6. An electrical connector according to claim 5 wherein the first terminal-engaging surface is generally cylindrically convex and the second terminal-engaging surface is generally cylindrically concave.

7. An electrical connector according to claim 6 further comprising retaining means for preventing separation of the actuator from the housing.

8. An electrical connector according to claim 7 wherein the retaining means comprises a lip at one end of the second terminal-engaging surface of the actuator for engaging one edge of the housing when the actuator is in its open position to prevent separation of the actuator from the housing.

9. An electrical connector according to claim 1 wherein the housing has forward and rearward edges, and the passageway extends substantially between the forward and rearward edges, the connector further comprising an aforesaid electric wire attached to one end of the actuator constituting the rearward end of the actuator, the cooperable positioning means being adapted for moving the actuator from its open position toward its wedged position as the actuator is moved generally longitudinally rearwardly so that the actuator may be moved to its wedged position by pulling the wire rearwardly.

10. An electrical connector according to claim 9 wherein the actuator and the housing are molded of an electrically-conductive polymer.

11. An electrical connector according to claim 1 wherein the actuator comprises a body of electrically-conductive material and means for attaching the electrical wire to the body, the wire-attaching means being adapted for a snap fit on the body to hold the wire between the wire-attaching means and the body.

12. An electrical connector according to claim 11 wherein the wire-attaching means is adapted for attaching electrical wires of the type having a central conductive core coated with an electrical-insulating layer, the wire-attaching means being formed of generally electrical conductive material, and including opposed blades spaced apart a distance no greater than the thickness of the conductive core and adapted to cut through the electrical-insulating layer to provide a conductive path between the wire and the second terminal-engaging surface.

13. An electrical connector according to claim 12 wherein the body and wire-attaching means are formed of carbon fiber reinforced polyphenylene sulfide material.

14. An electrical connector according to claim 12 further including retaining means for preventing separation of the actuator from the housing, the retaining means comprising portions associated with the blades of the wire-attaching means extending beyond the second terminal-engaging surface of the actuator for engaging one edge of the housing when the actuator is in its open position.

* * * * *